(12) United States Patent
Kolb et al.

(10) Patent No.: US 6,562,944 B1
(45) Date of Patent: May 13, 2003

(54) AMIDE LIBRARY FORMATION USING A "BY-PRODUCT-FREE" ACTIVATION/ COUPLING SEQUENCE

(75) Inventors: Hartmuth C. Kolb, East Windsor, NY (US); Qun Sun, Belle Mead, NJ (US)

(73) Assignee: Lexicon Pharmaceuticals, New Brunswick, NJ (US)

( * ) Notice: Subject to any disclaimer, the term of this patent is extended or adjusted under 35 U.S.C. 154(b) by 0 days.

(21) Appl. No.: 09/532,490

(22) Filed: Mar. 22, 2000

Related U.S. Application Data

(60) Provisional application No. 60/127,600, filed on Mar. 23, 1999.

(51) Int. Cl.$^7$ ................................................. C07K 1/06
(52) U.S. Cl. ...................... 530/345; 530/333; 530/334; 530/335; 530/336; 530/337; 530/338; 530/344; 544/180; 544/183; 564/123; 564/161; 564/170; 546/347
(58) Field of Search ................................ 544/180, 183; 546/347; 564/161, 120, 123; 560/19; 530/333–338, 344, 345

(56) References Cited

U.S. PATENT DOCUMENTS 4,562,253 A * 12/1985 Prager et al. .................. 544/19
5,244,892 A * 9/1993 Suzue et al. ................. 514/206

OTHER PUBLICATIONS

Jiang et al., Tet. Lett. vol. 34, No. 42 (1993) pp. 6705–6708.*

Kim et al., J. Chem. Soc., Chem. (1985) p. 473.*

Gayo, L.M., et al., Tetrahedron Lett. 37:4915–18, 1996.

* cited by examiner

*Primary Examiner*—Bennett Celsa
(74) *Attorney, Agent, or Firm*—McDonnell Boehnen Hulbert & Berghoff

(57) ABSTRACT

Disclosed is an improved method for preparing an activated carboxylic acid in the form of a pentafluorophenyl ester, an improved method for making a carboxamide from a pentaflourophenyl ester, and a carboxamide and carboxamide library prepared using both of these methods.

13 Claims, No Drawings

AMIDE LIBRARY FORMATION USING A "BY-PRODUCT-FREE" ACTIVATION/COUPLING SEQUENCE

This application claims the benefit of U.S. Provisional Application No. 60/127,600, filed Mar. 23, 1999.

BACKGROUND OF THE INVENTION

1. Field of the Invention

This invention relates to adding a polymer-bound base as an improvement for the method of preparing an amide library by the by-product free generation of PFP esters.

2. Description of the Related Art

Pentafluorophenyl (PFP) esters are commonly used as activated intermediates for the generation of amides, which play a key role in biological and chemical systems (i.e. amides are the predominant functional groups of peptides and many organic molecules). Treatment of carboxylic acids, including N-protected amino acids with certain activated PFP esters under mild conditions results in the formation of these activated building blocks that can, in turn, be used to form internal or external amides.

PFP esters derived from carboxylic acids characterized by a low pKa can be used to prepare activated carboxylic acids via a mixed anhydride intermediate. Pentafluorophenyl trifluoroacetate (PFP-TFA) is known to be an excellent PFP ester for the simultaneous protection and activation of carboxylic acids, including amino and thiol carboxylic acids. Gayo, L. M., Suto, M. J., *Tetrahedron Letters* 37, 4915-18 (1996). The treatment of carboxylic acids, with PFP-TFA in tetrahydrofuran or N,N-dimethylformamide at room temperature provides the corresponding trifluroracetyl-protected, pentafluorophenol-activated derivative. Other reagents such as 9-fluorenylmethylpentafluorophenyl carbonate or pentafluorophenyl acetate can also be used to form an activated PFP ester.

The major problem with the current methods of producing the PFP esters is that all require the presence of an organic base such as pyridine, present in as much as five equivalents. This results in the generation of by-products such as ureas and ammonium salts which can be difficult to remove. Further, such by-products hamper the synthesis, isolation and biological screening of biologically active compounds. For this reason, crude PFP esters must be chromatographed over silica gel or recrystalized to afford relatively pure product.

It is also desirable to find a simpler reaction system for preparing carboxamides than using 1-hydroxybenzotriazole hydrate (HOBT)/o-benzotriazol-1-yl-N,N,N',N'-tetramethyluronium hexafluorophosphate (HBTU). Further, the HOBT/HBTU system does not work well on hindered moieties, such as, for example, hindered indanols or furan contain amines.

It is therefore necessary to develop an improvement of the current methodologies that allows for the automated synthesis of amide libraries in solution phase without requiring laborious separation of by-products.

SUMMARY OF THE INVENTION

This invention provides for the improved method of preparing an activated carboxylic acid as the pentafluorophenyl (PFP) ester using pentafluorophenyl trifluoroacetate (PFP-TFA) in the presence of polyvinylpyridine and poly-DMAP (poly-4-dimethlyaminopyridine) (catalyst). This invention also provides for the improved method of coupling the activated ester with a nucleophile, e.g. amines and thiols, in the presence of polymeric reagents and catalysts. The invention further provides for the preparation of carboxamides and carboxamide libraries using the improved method of preparing an activated carboxylic acid as the pentafluorophenyl (PFP) ester using PFP-TFA in the presence of polyvinylpyridine and poly-DMAP (catalyst). The invention further provides for the preparation of carboxamides and carboxamide libraries using the improved method of coupling the activated ester with a nucleophile, e.g. amines and thiols, in the presence of polymeric reagents and catalysts. For example, known compounds such as the anticholinergic agent N-(1,2-diphenylethyl)nicotinamide (I) can be prepared using the method of the present invention.

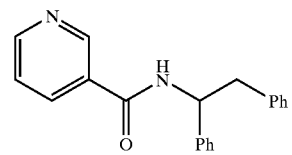

I

In yet another embodiment, this invention provides for the improved method of preparing a carboxamide by generating a PFP ester using pentafluorophenyl diphenylphosphinate (PFP-DPP)/dimethyl formamide (DMF) in the presence of a resin and subsequently treating such ester with an amine in the presence of a suitable base.

DETAILED DESCRIPTION OF THE INVENTION

The present invention relates to an improved method of activating carboxylic acids as the pentafluorophenyl (PFP) ester using PFP-TFA in the presence of polyvinylpyridine and poly-DMAP (catalyst). Removal of the excess reagent by filtration and evaporation is easily achieved. No chromatography or recrystalization is required with this improved method.

The present invention also relates to an improved method for making a carboxamide by treating a PFP ester with an amine in the presence of polymeric reagents and catalysts, used to remove excess reagent. For example, excess reagent can be removed using scavenger resins, e.g. polymeric amine resins, if the intermediate PFP ester is used in excess, or poly-isocyanate or acidic ion exchange resin, if the amine is used in excess. Thus, the use of polymeric reagents and catalysts ensures easy work-up and provides extremely pure products.

An illustration of an embodiment of the invention is given in Scheme I.

Scheme I

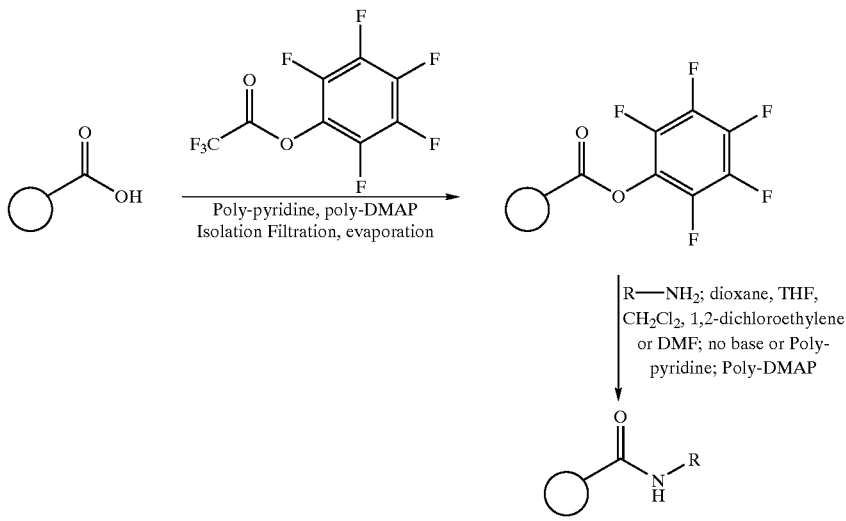

The invention further provides for the preparation of carboxamides and carboxamide libraries using the improved method of preparing an activated carboxylic acid as the pentafluorophenyl (PFP) ester using PFP-TFA in the presence of polyvinylpyridine and poly-DMAP (catalyst). The invention further provides for the preparation of carboxamides and carboxamide libraries using the improved method of coupling the activated ester with a nucleophile, e.g. amines, in the presence of polymeric reagents and catalysts.

The present invention further relates to an improved method of preparing a carboxamide by generating a PFP ester using pentafluorophenyl diphenylphosphinate (PFP-DPP)/dimethyl formamide (DMF) in the presence of a resin such polyvinylpyridine and subsequently treating such ester with an amine in the presence of a base, such as, for example, a tertiary amine. A preferred embodiment of this method is the preparation of a carboxamide on a heterocyclic ring such as an oxazole,or a furan. Another preferred embodiment of this method is the use of disopropyethylamine as the tertiary base. An illustration of this method is depicted in Scheme II.

Scheme II

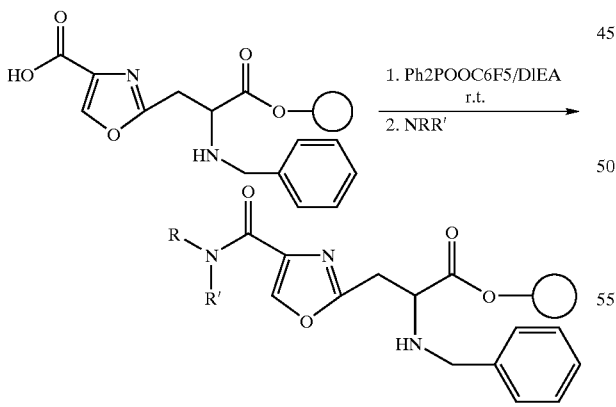

wherein R and R' are the same or different and represent hydrogen or an organic chemistry group.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

Representative examples of methods for preparing intermediates of the invention are set forth below.

EXAMPLES

Example 1

Scheme III

1. PFP Ester Formation

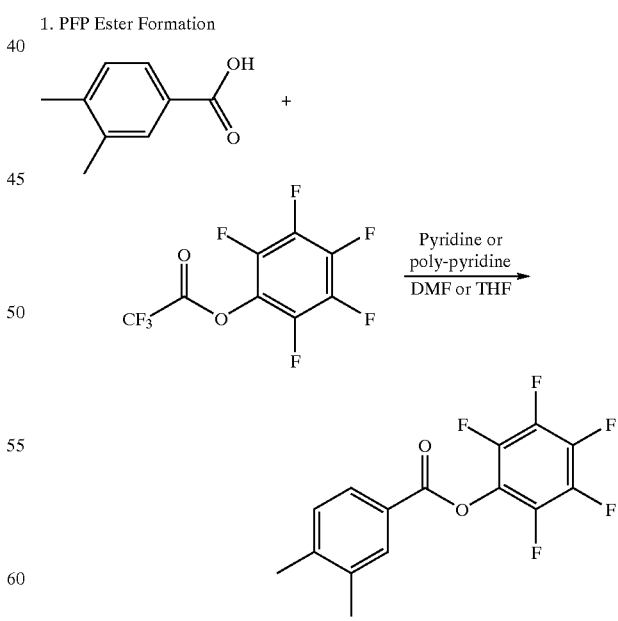

Six reaction conditions are used for the PFP activation reaction (cf Table 1). In all six reactions, 2 mmol 3,4-dimethylbenzoic acid is reacted with of 10 mmol pentafluorophenyl trifluoroacetate.

TABLE 1

| Entry | Reaction Condition | Result |
|---|---|---|
| 1 | 10 mmol pyridine, 2.5 ml DMF | completed in 2 h |
| 2 | 10 mmol pyridine, 2.5 ml THF | completed in 2 h |
| 3 | 10 mmol polymer-pyridine, DMF | completed in 2 h |
| 4 | 10 mmol polymer-pyridine, 0.4 mmol polymer-DMAP, THF | less than 10% product overnight |
| 5 | 10 mmol polymer-pyridine, 0.4 mmol polymer-DMAP, THF/CH$_2$Cl$_2$(1:1) | less than 30% product overnight |
| 6 | 10 mmol polymer-pyridine, 0.4 mmol polymer-DMAP, THF/CH$_3$CN(1:1) | completed overnight |

The reaction mixture in Entry 6 is stirred overnight and then filtered to remove the polymers. The residue is washed with the solvent used in the reaction and the combined filtrates are concentrated in vacuum. Xylene (10 ml) is added, and the solution is concentrated in vacuum (4x). The residue is dried under high vacuum overnight to give ester (590 mg, 93%). NMR shows over 90% purity of crude product.

The above results show that solid reagents can be successfully employed for the preparation of PFP esters. The reaction is solvent dependent, and best results are achieved in 1:1 THF/CH$_3$CN (entry 6).

2. Carboxamide Formation

Two amines (benylamine and indanolamine, 1 equivalent) are reacted with the PFP ester in THF (Schemes IV and V). All six reactions are very sluggish in the absence of a base. Addition of a tertiary amine base considerably accelerates the reaction. Polymer-bound diisopropylethylamine (DIEA) proves to be a useful catalyst for this reaction (see table 2). The reactions are completed after 12 hours. Excess reagents are removed by addition of two equivalents of scavenger resins—polymer-bound isocyanate (reaction 1 and 3) and polymer-bound tris(2-aminoethyl)amine (reaction 2 and 4)—and by continuing to stir for another 12 hours. Filtration of the reaction mixtures and evaporation of the filtrates provides the crude products. The latter are analyzed by LC/MS and NMR (table 3).

Scheme IV

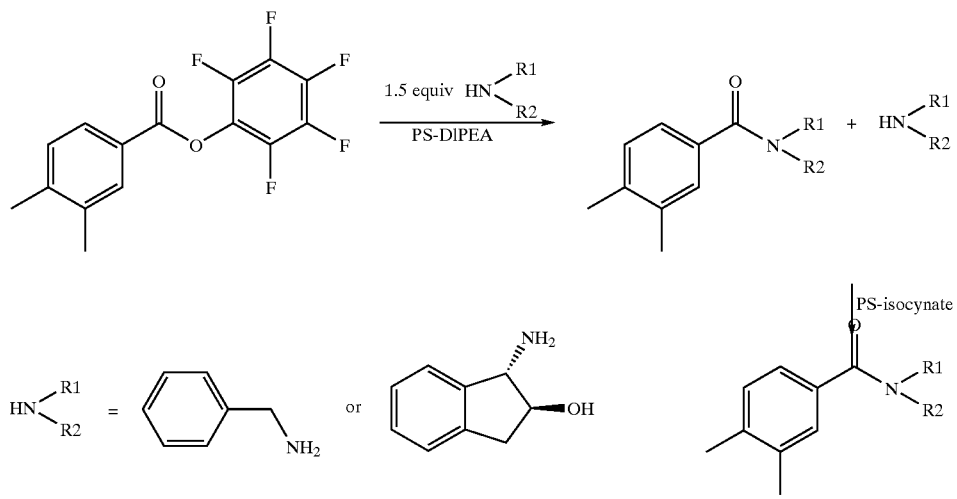

Scheme V

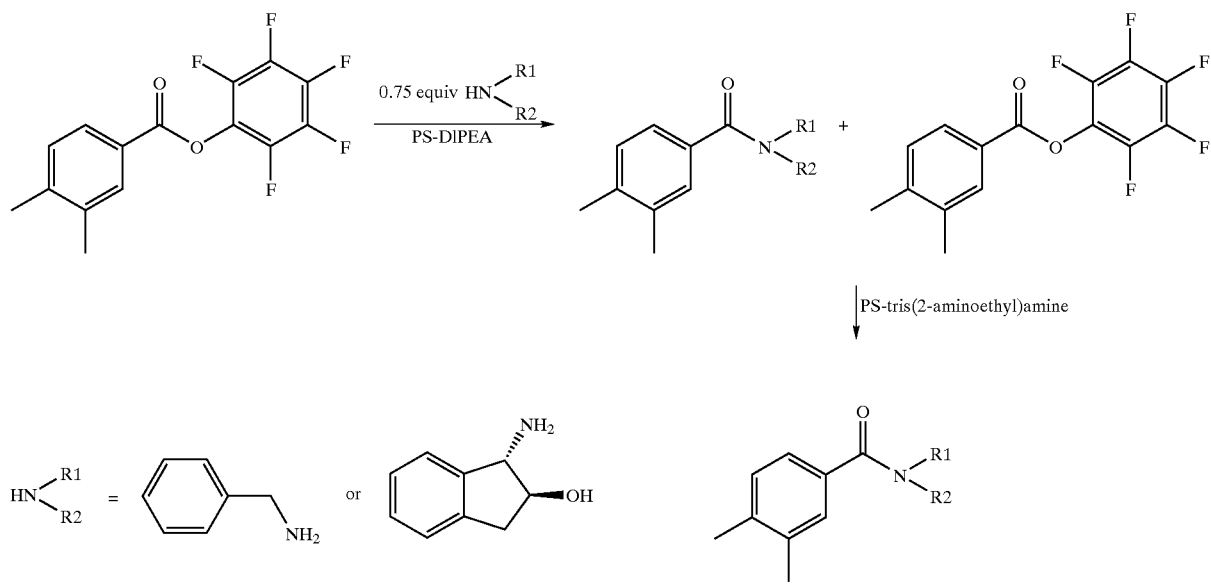

TABLE 2

| Entry | Amines | Polymer-DIPEA | Solvent |
|---|---|---|---|
| 1 | Benzylamine (1.5 eq) | 1.5 eq | THF |
| 2 | Benzylamine (0.75 eq) | 1 eq | THF |
| 3 | trans-1-amino-2-indanol (1.5 eq) | 1.5 eq | THF |
| 4 | trans-1-amino-2-indanol (0.75 eq) | 1 eq | THF |

TABLE 3

| Entry | LC/DAD Purity | LC/MS Purity | NMR Purity |
|---|---|---|---|
| 1 | 96% | 96% | >80% main contaminant: benzylamine |
| 2 | 99% | 100% | >95% |
| 3 | 89% amide + 6.5% ester | 62% amide + 36% ester | >80% |
| 4 | 91% amide + 3.7% ester | 59% amide + 26% ester | >80% |

The above results show that polymeric reagents and catalysts can be used, both for the formation of PFP esters and for their coupling with amines. Polymeric reagents have the advantage that by-products can be readily removed by filtration. This greatly simplifies the work-up and it enhances the purity of the products.

Example 2

About 20 mg of resin (~12 umol) is charged with 350 ul of pentafluorophenyl diphenylphosphinate/DMF stock solution (C=0.344 M, 10 eq.), 83.5 ul of polymer-bound DIEA (40 eq) and 10 eq. of an amine. The mixture is shaken on orbital shaker at 200 rpm overnight. The resin is drained and washed with DMF, THF, and DCM. The results are depicted in Table 4.

TABLE 4

| Compound | Purity (LC) | Purity (MS) |
|---|---|---|
| 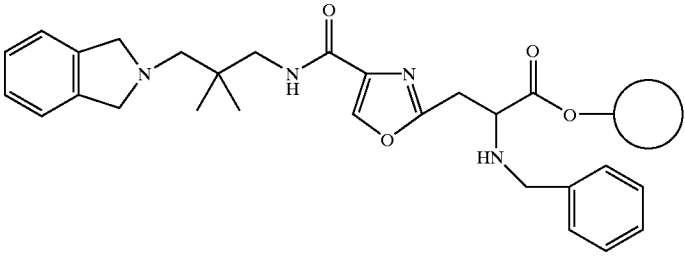 | 91% | 95% |
| 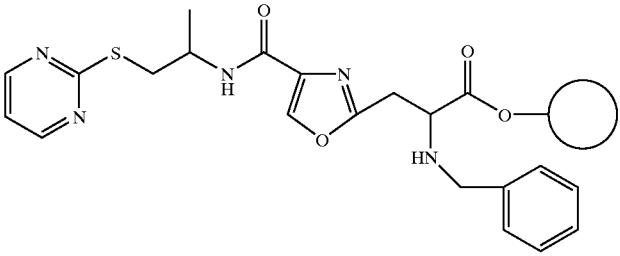 | 98% | 95% |
| 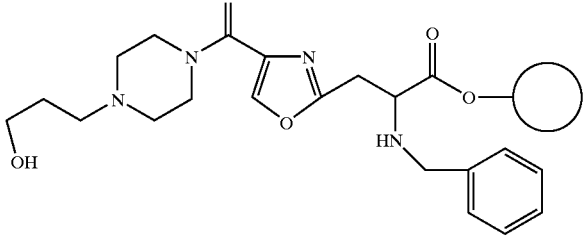 | 82% | 83%; two peaks show same MS |

TABLE 4-continued

| Compound | Purity (LC) | Purity (MS) |
|---|---|---|
| | 90% | 90% |
| | 96% | 91% |
| | 70% | 65% |
| | 98% | 90%; two peaks show same MS |
| | 95% | 90% |

TABLE 4-continued

| Compound | Purity (LC) | Purity (MS) |
|---|---|---|
| [structure] | 69% | 81%; no SM, one major prod. Peak |
| [structure] | 60% | 63%; no SM, some small unknown peaks |
| [structure] | 58% | 79%; no SM, two small uv peaks did not show MS |

Example 3

For furan moiety containing compounds, 10% TFA/DCM condition is recommended for cleavage from resin since furan moiety may not be stable in very harsh acidic conditions. Typical cleavage condition (TFA/DCM=1/1), as known in the art, is used for all other cleavage except furan containing compounds.

The invention and manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. In a method for making a PFP ester by treating a carboxylic acid with a fluorinated carboxylic PFP ester, the improvement comprising adding a first polymer-bound base and a catalytic amount of a second polymer bound base.

2. The method according to claim 1, wherein the carboxylic acid is treated with the fluorinated carboxylic PFP ester in the presence of the first polymer-bound base and the second polymer bound base in at least one solvent.

3. The method according to claim 2, wherein the fluorinated carboxylic PFP ester is pentafluorophenyl trifluoroacetate.

4. The method according to claim 2, wherein the first polymer-bound base is polymer-bound pyridine.

5. The method according to claim 4, wherein 5 equivalents of polymer-bound pyridine is added.

6. The method according to claim 2, wherein the solvent is dimethylformamide.

7. The method according to claim 2, further comprising purifying the PFP ester.

8. The method according to claim 7, wherein purifying the PFP ester comprises (a) filtrating the carboxylic acid/fluorinated carboxylic PFP ester/polymer-bound base mixture to isolate a residue without the polymer bound base;

(b) washing the residue with more of the solvent; and (c) evaporating the solvent to afford the PFP ester.

9. The method according to claim 1, wherein the second polymer bound base is polymer bound DMAP.

10. The method according to claim 9, wherein the polymer bound DMAP is present in an amount of about 20 mol%.

11. The method according to claim 2, wherein the at least one solvent is a mixture of two solvents.

12. The method according to claim 11, wherein one of the two solvents is tetrahydrofuran.

13. The method according to claim 11, wherein the mixture is 1:1 tetrahydrofuran and acetonitrile.

* * * * *